(12) United States Patent
Yoshida

(10) Patent No.: US 10,939,880 B2
(45) Date of Patent: Mar. 9, 2021

(54) X-RAY FLUOROSCOPIC IMAGING APPARATUS

(71) Applicant: SHIMADZU CORPORATION, Kyoto (JP)

(72) Inventor: Koji Yoshida, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 35 days.

(21) Appl. No.: 16/653,168

(22) Filed: Oct. 15, 2019

(65) Prior Publication Data

US 2020/0289068 A1 Sep. 17, 2020

(30) Foreign Application Priority Data

Mar. 11, 2019 (JP) .............. JP2019-044007

(51) Int. Cl.
| | | |
|---|---|---|
| A61B 6/00 | (2006.01) | |
| H01H 3/02 | (2006.01) | |
| H01H 3/22 | (2006.01) | |
| A61B 6/10 | (2006.01) | |
| H01H 13/807 | (2006.01) | |

(52) U.S. Cl.
CPC .............. *A61B 6/105* (2013.01); *A61B 6/467* (2013.01); *A61B 6/487* (2013.01); *H01H 3/022* (2013.01); *H01H 13/807* (2013.01); H01H 2217/004 (2013.01); H01H 2223/034 (2013.01); H01H 2239/03 (2013.01)

(58) Field of Classification Search
CPC ......... A61B 6/105; A61B 6/467; A61B 6/487; H01H 3/022; H01H 13/807; H01H 13/84; H01H 2217/004; H01H 2223/034; H01H 2225/022; H01H 2239/03; H01H 2300/014

See application file for complete search history.

(56) References Cited

U.S. PATENT DOCUMENTS

| | | | | |
|---|---|---|---|---|
| 4,170,735 A | * | 10/1979 | Codina ................... | H05G 1/06 378/96 |
| 5,832,056 A | * | 11/1998 | Mochitate ............ | A61B 6/0487 378/195 |
| 7,177,393 B2 | | 2/2007 | Kanemitsu | |
| 2005/0133348 A1 | * | 6/2005 | Berthaud ............... | H01H 9/282 200/50.01 |
| 2008/0217564 A1 | * | 9/2008 | Beyar ...................... | A61B 6/00 250/515.1 |
| 2012/0071752 A1 | * | 3/2012 | Sewell ................... | A61B 34/74 600/424 |
| 2013/0202086 A1 | * | 8/2013 | Tsuji ........................ | G01T 1/02 378/62 |

(Continued)

FOREIGN PATENT DOCUMENTS

| | | |
|---|---|---|
| JP | 2005-102937 | 4/2005 |
| JP | 2006-55633 | 3/2006 |

*Primary Examiner* — Mark R Gaworecki
(74) *Attorney, Agent, or Firm* — Andrew F. Young, Esq.; Nolte Lackenbach Siegel

(57) ABSTRACT

An X-ray fluoroscopic imaging apparatus includes a table, an imaging system including an X-ray source and a detector, and an operation panel unit including a plurality of operation input units. The plurality of operation input units include an emergency stop unit and a stop state release unit. The emergency stop unit and the stop state release unit are provided separately from each other at different positions.

9 Claims, 6 Drawing Sheets

(56) References Cited

U.S. PATENT DOCUMENTS

| | | | |
|---|---|---|---|
| 2013/0317519 A1* | 11/2013 | Romo | A61B 90/06 606/130 |
| 2014/0155728 A1* | 6/2014 | Lee | A61B 5/0555 600/407 |
| 2015/0179368 A1* | 6/2015 | Roe | H01H 9/287 200/334 |
| 2017/0150934 A1* | 6/2017 | Bennett | A61B 6/037 |
| 2018/0242935 A1* | 8/2018 | Bouvier | A61B 6/102 |

* cited by examiner

FIRST MODIFIED EXAMPLE

SECOND MODIFIED EXAMPLE

THIRD MODIFIED EXAMPLE

X-RAY FLUOROSCOPIC IMAGING APPARATUS

CROSS-REFERENCE TO RELATED APPLICATIONS

This application claims the benefit of priority to Japanese Patent Application No. 2019-044007 filed on Mar. 11, 2019, the entire contents of which are hereby fully incorporated by reference.

BACKGROUND OF THE INVENTION

Field of the Invention

The present invention relates to an X-ray fluoroscopic imaging apparatus, and more particularly, it relates to an X-ray fluoroscopic imaging apparatus including an emergency stop unit configured to urgently stop movement of a table and an imaging system.

Description of the Background Art

Conventionally, an X-ray fluoroscopic imaging apparatus including an emergency stop unit configured to urgently stop movement of a table and an imaging system is known. Such an X-ray fluoroscopic imaging apparatus is disclosed in Japanese Patent Laid-Open No. 2006-055633, for example.

Japanese Patent Laid-Open No. 2006-055633 discloses an X-ray imaging apparatus including a bed, an X-ray irradiation means, an X-ray detection means, an operation means, and a top board moving mechanism (table moving mechanism). The X-ray irradiation means is provided under the bed. The X-ray irradiation means and the X-ray detection means face each other with a subject interposed therebetween. The operation means is provided on the X-ray detection means.

The X-ray imaging apparatus disclosed in Japanese Patent Laid-Open No. 2006-055633 is configured to be able to move the top board of the bed (table) with the top board moving mechanism, and is configured to be able to move the operation means. The X-ray imaging apparatus disclosed in Japanese Patent Laid-Open No. 2006-055633 moves the top board with the top board moving mechanism and moves the operation means, and captures a fluoroscopic image of the subject. Furthermore, in the X-ray imaging apparatus disclosed in Japanese Patent Laid-Open No. 2006-055633, an emergency stop unit configured to urgently stop the operations of the X-ray irradiation means, the top board moving mechanism, and the operation means is provided on the bed.

The emergency stop unit needs to be configured to take an emergency stop operation and an operation of releasing a stop state as different intentional operations based on the safety standards. Therefore, although not disclosed in Japanese Patent Laid-Open No. 2006-055633, conventionally, a so-called mushroom-shaped push button configured to enable two different types of operations with one button is provided as an emergency stop unit. The mushroom-shaped push button is configured to receive an input for emergency stop by being pressed, and is configured to receive an input for releasing a stop state by being twisted (rotated).

In order to enable an emergency stop operation by pressing and a release operation by twisting (rotating), the emergency stop unit includes a mechanism configured to lock movement of the button when the button is pressed, and a mechanism configured to unlock the button when the button is twisted (rotated). Therefore, when the push button configured to enable two different types of operations is used as the emergency stop unit, the protruding height of the emergency stop unit is disadvantageously increased. When the protruding height of the emergency stop unit is increased, it becomes difficult to thin an operation panel unit provided with the emergency stop unit.

SUMMARY OF THE INVENTION

The present invention has been proposed in order to solve the aforementioned problems, and an object of the present invention is to provide an X-ray fluoroscopic imaging apparatus in which an operation panel unit provided with an emergency stop unit can be thinned.

In order to attain the aforementioned object, an X-ray fluoroscopic imaging apparatus according to an aspect of the present invention includes a table on which a subject is placed, an imaging system including an X-ray source configured to irradiate the subject with X-rays and a detector configured to detect the X-rays emitted from the X-ray source and transmitted through the subject, and an operation panel unit including a plurality of operation input units configured to receive operation inputs for operating the imaging system. The plurality of operation input units include an emergency stop unit configured to receive an operation input for urgently stopping movement of the table and the imaging system, and a stop state release unit configured to receive an operation input for releasing stop states of the table and the imaging system, and the emergency stop unit and the stop state release unit are provided separately from each other at different positions. In this specification, the term "emergency stop" indicates forcibly stopping movement of the table and movement of the imaging system in an emergency.

In the X-ray fluoroscopic imaging apparatus according to this aspect of the present invention, as described above, the emergency stop unit and the stop state release unit are provided separately from each other at the different positions. Accordingly, the emergency stop unit and the stop state release unit are provided separately from each other such that each of the emergency stop unit and the stop state release unit can be configured as a simply structured operation input unit configured to receive an operation input only through a single operation. Consequently, it is possible to reduce the protruding height of each of the emergency stop unit and the stop state release unit as compared with a single operation input unit that enables two different types of operations. Therefore, the operation panel unit including the emergency stop unit can be thinned. Even with this structure, the emergency stop unit and the stop state release unit disposed at the different positions are operated separately, and thus the requirement that an emergency stop operation and an operation of releasing the stop state be taken as different intentional operations can be met.

In the aforementioned X-ray fluoroscopic imaging apparatus according to this aspect, each of the emergency stop unit and the stop state release unit is preferably a push button configured to receive a single operation, the operation panel unit preferably includes a surrounding region around the emergency stop unit and a surrounding region around the stop state release unit, and a pressed surface of the emergency stop unit and a pressed surface of the stop state release unit are preferably respectively provided at positions recessed with respect to the surrounding regions in a direction that intersects with a surface of the operation panel unit. Accordingly, the pressed surface of the emergency stop unit and the pressed surface of the stop state release unit are disposed at the positions recessed with respect to the surrounding regions such that unintentional contact of the operator with the emergency stop unit and the stop state release unit can be significantly reduced or prevented. Consequently, an unintentional emergency stop operation by the operator can be significantly reduced or prevented, and an unintentional operation of releasing the stop state by the operator can be significantly reduced or prevented. Although each of the emergency stop unit and the stop state release unit is configured to receive a single operation, the emergency stop unit and the stop state release unit are provided at the different positions such that the safety standards in which different intentional operations are required can be met. Note that the term "push button configured to receive a single operation" indicates a button configured to output a signal for performing a predetermined operation while pressed by the operator and to stop the output of the signal for performing the predetermined operation when the operator releases the button. Furthermore, the "push button configured to receive a single operation" may be a button configured to output the signal for performing the predetermined operation when the operator does not touch the button and to stop the output of the signal for performing the predetermined operation when the operator presses the button. That is, the "push button configured to receive a single operation" is a so-called self-return button.

In this case, the surrounding regions preferably protrude with respect to the surface of the operation panel unit outside the surrounding regions. According to this structure, the surrounding regions protrude with respect to the surface of the operation panel unit outside the surrounding regions, and thus the emergency stop unit and the stop state release unit are disposed on the surface of the operation panel unit inside the surrounding regions such that the pressed surface of the emergency stop unit and the pressed surface of the stop state release unit can be easily disposed at the positions recessed with respect to the surrounding regions.

In the aforementioned structure in which the operation panel unit includes the surrounding regions around the emergency stop unit and the stop state release unit, the surrounding regions are preferably recessed toward a back surface side with respect to the surface of the operation panel unit outside the surrounding regions. According to this structure, the surrounding regions are recessed toward the back surface side with respect to the surface of the operation panel unit outside the surrounding regions, and thus the emergency stop unit and the stop state release unit are disposed inside the surrounding regions such that a pressed surface of the emergency stop unit and a pressed surface of the stop state release unit can be disposed at positions recessed from the surface of the operation panel unit. Consequently, the pressed surface of the emergency stop unit and the pressed surface of the stop state release unit can be easily disposed at the positions recessed from the surrounding regions. Furthermore, the emergency stop unit and the stop state release unit can be disposed at the positions recessed from the surface of the operation panel unit, and thus as compared with the case in which the emergency stop unit and the stop state release unit are provided at positions that protrude from the surface of the operation panel unit, an erroneous operation can be further significantly reduced or prevented.

In the aforementioned X-ray fluoroscopic imaging apparatus according to this aspect, the operation panel unit preferably includes a first operation panel integrally provided on a moving unit of the imaging system, which is movable with respect to the table, and in the first operation panel, the emergency stop unit and the stop state release unit are preferably operation input units disposed on an outermost side among the plurality of operation input units. According to this structure, it is possible to reduce the protruding height of each of the emergency stop unit and the stop state release unit as compared with a single operation input unit that enables two different types of operations, and thus the emergency stop unit and the stop state release unit can be provided on the moving unit having a limited space in which the operation input units are disposed. Consequently, when the imaging system moves, the emergency stop unit and the stop state release unit can be operated. In addition, the emergency stop unit and the stop state release unit are the operation input units disposed on the outermost side among the plurality of operation input units such that unintentional contact of the hand (fingers) of the operator who operates the operation input units in order to capture an X-ray fluoroscopic image with the emergency stop unit and the stop state release unit can be significantly reduced or prevented when the X-ray fluoroscopic image is captured. Consequently, unintentional operations on the emergency stop unit and the stop state release unit by the operator can be significantly reduced or prevented when the X-ray fluoroscopic image is captured.

In this case, the plurality of operation input units are preferably disposed in a plurality of rows in a direction that intersects with a longitudinal direction of the first operation panel in a plane of the first operation panel, and the emergency stop unit and the stop state release unit are preferably disposed in an outermost row of the plurality of rows in which the plurality of operation input units are disposed. According to this structure, unintentional contact of the hand (fingers) of the operator who operates the operation input units in order to capture an X-ray fluoroscopic image with the emergency stop unit and the stop state release unit can be easily significantly reduced or prevented when the X-ray fluoroscopic image is captured. Consequently, unintentional operations on the emergency stop unit and the stop state release unit by the operator can be further significantly reduced or prevented when the X-ray fluoroscopic image is captured.

The aforementioned structure in which the operation panel unit includes the first operation panel integrally provided on the moving unit movable with respect to the table preferably further includes a main body configured to hold the table, the operation panel unit preferably includes a second operation panel provided on the main body, and in the second operation panel, the emergency stop unit and the stop state release unit are preferably the operation input units disposed on the outermost side among the plurality of operation input units. According to this structure, not only with the first operation panel but also with the second operation panel, an operation input for urgently stopping the X-ray fluoroscopic imaging apparatus can be performed. Consequently, an operation of urgently stopping the X-ray fluoroscopic imaging apparatus and an operation of releasing the stop state can be performed with the operation panel closer to the operator among the first operation panel and the second operation panel, and thus the convenience of the operator can be improved. Furthermore, in the second operation panel, the emergency stop unit and the stop state release unit are the operation input units provided on the outermost side among the plurality of operation input units such that unintentional contact of the hand (fingers) of the operator who operates the operation input units in order to capture an X-ray fluoroscopic image with the emergency stop unit and the stop state release unit can be significantly reduced or prevented when the X-ray fluoroscopic image is captured. Consequently, unintentional operations on the emergency stop unit and the stop state release unit by the operator in the second operation panel can be significantly reduced or prevented.

In the aforementioned X-ray fluoroscopic imaging apparatus according to this aspect, at least the emergency stop unit of the emergency stop unit and the stop state release unit is preferably distinguishably different in at least one of color and shape from remaining operation input units. According to this structure, the emergency stop unit can be easily distinguished from the remaining operation input units. Consequently, when the operator performs an emergency stop operation, the emergency stop unit can be distinguished from the remaining operation input units at a glance, and thus the emergency stop operation can be reliably performed.

In this case, the emergency stop unit and the stop state release unit are preferably distinguishably different in at least one of color and shape from each other. According to this structure, the emergency stop unit and the stop state release unit can be easily distinguished from each other. Consequently, when the operator performs an emergency stop operation, the emergency stop unit and the stop state release unit can be distinguished from each other at a glance, and thus the emergency stop operation can be more reliably performed.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of the present invention is hereinafter described with reference to the drawings.

The structure of an X-ray fluoroscopic imaging apparatus 100 according to the embodiment is now described with reference to FIGS. 1 to 6.

(Structure of X-ray Fluoroscopic Imaging Apparatus)

Figure 1:
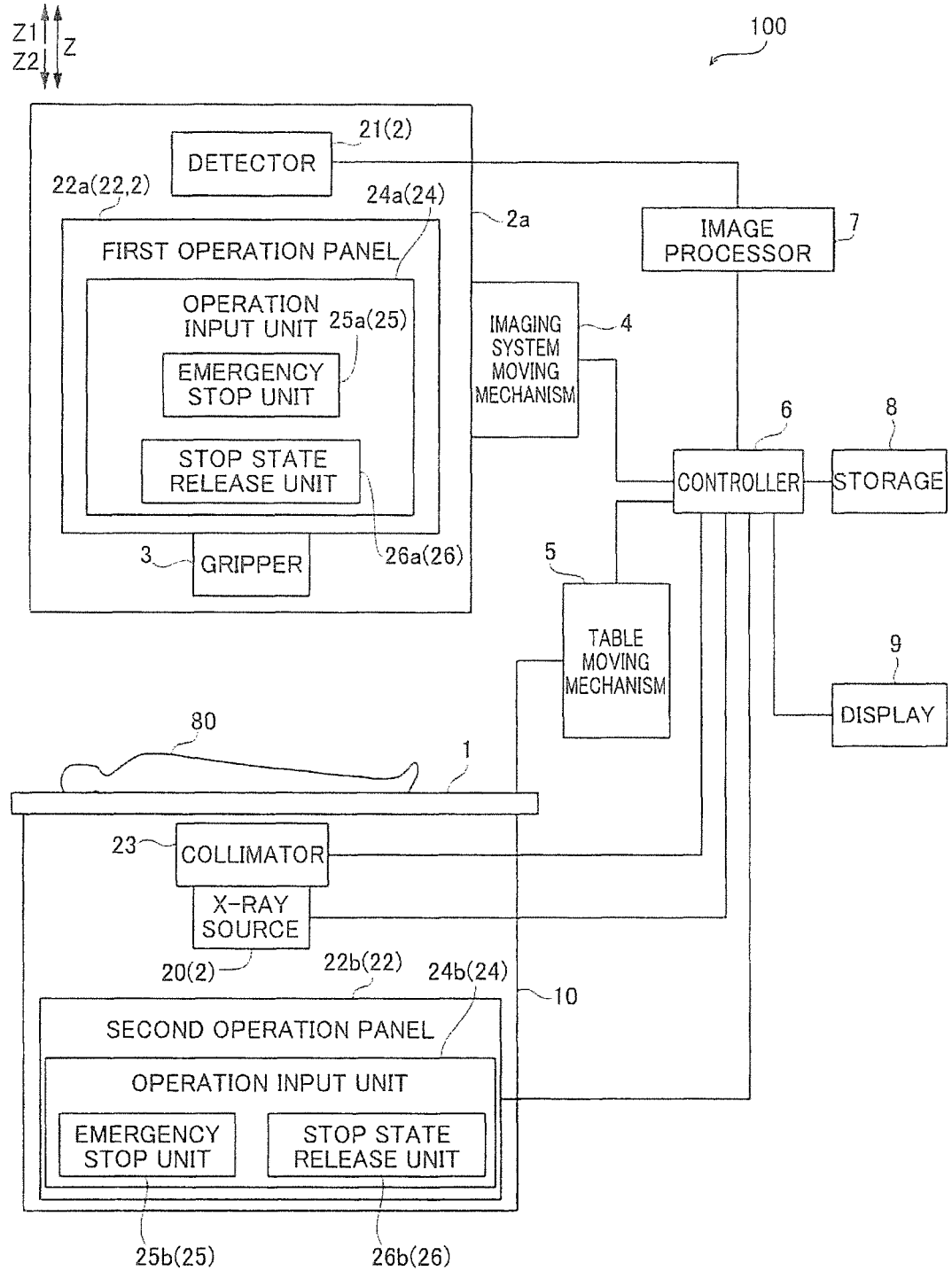
FIG. 1 is a block diagram showing the overall structure of an X-ray fluoroscopic imaging apparatus according to an embodiment.

As shown in FIG. 1, the X-ray fluoroscopic imaging apparatus 100 according to this embodiment includes a table 1, an imaging system 2, a gripper 3, an imaging system moving mechanism 4, a table moving mechanism 5, a controller 6, an image processor 7, and a storage 8. Furthermore, in an example shown in FIG. 1, the controller 6 of the X-ray fluoroscopic imaging apparatus 100 is connected to a display 9.

A subject 80 is placed on the table 1. The table 1 is held by a main body 10. The table 1 has a rectangular flat plate shape in a plan view. The subject 80 is placed on the table 1 in such a manner that the head-foot direction of the subject 80 is along the long side of the rectangular shape and the right-left direction of the subject 80 is along the short side of the rectangular shape. In this specification, a vertical direction is taken as a Z direction, an upward direction is taken as a Z1 direction, and a downward direction is taken as a Z2 direction. Two directions orthogonal to each other in a horizontal direction are taken as an X direction and a Y direction. In the X direction, a direction toward one side is taken as an X1 direction, and a direction toward the other side is taken as an X2 direction. Furthermore, in the Y direction, a direction toward one side is taken as a Y1 direction, and a direction toward the other side is taken as a Y2 direction. In the example shown in FIG. 1, the subject 80 is placed in such a manner that the head of the subject 80 is directed in the X1 direction. The head-foot direction of the subject 80 is a direction along a straight line that connects the head and the foot of the subject 80 to each other. That is, the X direction is the longitudinal direction of the table 1, and the Y direction is the short-side direction of the table 1.

The imaging system 2 includes an X-ray source 20, a detector 21, and an operation panel unit 22. The imaging system 2 is configured to capture an X-ray fluoroscopic image by detecting X-rays emitted from the X-ray source 20 to the subject 80 by the detector 21. The X-ray source 20 is configured to irradiate the subject 80 with X-rays due to a voltage applied by an X-ray tube drive (not shown). Moreover, the X-ray source 20 is provided in the Z2 direction side. The detector 21 is provided on the Z1 direction side. That is, the X-ray source 20 and the detector 21 face each other with the table 1 interposed therebetween. In addition, the X-ray source 20 includes a collimator 23 configured to be able to adjust an X-ray irradiation field, which is an X-ray irradiation range.

The collimator 23 is disposed between the X-ray source 20 and the detector 21. The collimator 23 is configured to be able to block X-rays. The collimator 23 is configured to be able to adjust the X-ray irradiation range by partially blocking the X-rays emitted from the X-ray source 20. The collimator 23 contains heavy metal such as lead, gold, or tungsten.

The detector 21 is configured to detect X-rays emitted from the X-ray source 20 and transmitted through the subject 80. The detector 21 includes a flat panel detector (FPD) or an image intensifier (II), for example. The detector 21 includes a plurality of conversion elements (not shown) and pixel electrodes (not shown) disposed on the plurality of conversion elements. The plurality of conversion elements and the pixel electrodes are arranged in an array on a detection surface at a predetermined cycle (pixel pitch). The detector 21 is also configured to output an acquired image signal to the image processor 7.

The gripper 3 is gripped when an operator 81 (see FIG. 2) moves the imaging system 2. That is, the operator 81 moves the imaging system 2 by applying a force in a direction in which the imaging system 2 is to be moved while gripping the gripper 3. The gripper 3 is made of a resin, for example. In this embodiment, the operator 81 is a doctor or a technician, for example.

The operation panel unit 22 includes a plurality of operation input units 24 configured to receive operation inputs for operating the imaging system 2. The plurality of operation input units 24 include an emergency stop unit 25 and a stop state release unit 26. The emergency stop unit 25 is configured to be able to receive an operation input for urgently stopping movement of the table 1 and the imaging system 2. The stop state release unit 26 is configured to be able to receive an operation input for releasing the stop states of the table 1 and the imaging system 2. Among the plurality of operation input units 24, operation input units 24 other than the emergency stop unit 25 and the stop state release unit 26 are configured to be able to receive operation inputs for movement of the table 1, adjustment of the X-ray irradiation range, etc. into the imaging system 2 required when an X-ray fluoroscopic image is captured.

The operation panel unit 22 also includes a first operation panel 22a and a second operation panel 22b. The first operation panel 22a is integrally provided on a moving unit 2a of the imaging system 2, which is movable with respect to the table 1. The second operation panel 22b is provided on the main body 10.

The imaging system moving mechanism 4 movably holds the imaging system 2. The imaging system moving mechanism 4 is configured to move the imaging system 2 in a direction in which the operator 81 applies a force to the gripper 3 under control of the controller 6. Furthermore, the imaging system moving mechanism 4 is configured to move the imaging system 2 based on operations (remote operations) performed by the operator 81 on the operation input units 24 or a console (not shown) provided at a position different from that of the X-ray fluoroscopic imaging apparatus 100. The imaging system moving mechanism 4 includes linear movement mechanisms respectively movable in the X direction, the Y direction, and the Z direction, and is configured to be able to move the imaging system 2 in the respective directions. The imaging system moving mechanism 4 also includes linear movement mechanisms configured to be able to move the X-ray source 20 in the X direction and the Y direction, and is configured to be able to move the X-ray source 20 in the X direction and the Y direction. The linear movement mechanisms of the imaging system moving mechanism 4 for the respective directions are belt pulley mechanisms each including a drive motor (not shown), a pair of rollers (not shown), and a timing belt (not shown), for example.

The table moving mechanism 5 is configured to move the table 1 so as to change the relative position of the table 1 to the imaging system 2 under control of the controller 6. Specifically, the table moving mechanism 5 is configured to be able to move the table 1 in the X direction and the Y direction so as to change the relative position between the table 1 and the imaging system 2. The table moving mechanism 5 includes linear movement mechanisms respectively movable in the X direction and the Y direction. The linear movement mechanisms of the table moving mechanism 5 for the respective directions are belt pulley mechanisms each including a drive motor (not shown), a pair of rollers (not shown), and a timing belt (not shown), for example.

The controller 6 is configured or programmed to control the imaging system moving mechanism 4 to move the imaging system 2. Furthermore, the controller 6 is configured or programmed to control the table moving mechanism 5 to move the table 1 relative to the imaging system 2. The controller 6 is also configured or programmed to control the collimator 23 to adjust the X-ray irradiation range. The controller 6 is a computer including a central processing unit (CPU), a read only memory (ROM), a random access memory (RAM), etc.

The image processor 7 is configured to generate an X-ray fluoroscopic image based on image information acquired by the imaging system 2. Specifically, the image processor 7 is configured to generate an X-ray fluoroscopic image as a moving image. The X-ray fluoroscopic image generated in the image processor 7 is displayed on the display 9. The image processor 7 includes a processor such as a graphics processing unit (GPU) or a field-programmable gate array (FPGA) configured for image processing.

The display 9 is configured as a liquid crystal display, for example. The display 9 is configured to display the X-ray fluoroscopic image generated by the image processor 7 based on the image information captured by the imaging system 2.

The storage 8 includes a hard disk drive (HDD) and a non-volatile memory, for example. The storage 8 is configured to be able to store the image information captured by the imaging system 2, the X-ray fluoroscopic image generated by the image processor 7, etc.

(Adjustment of Imaging System at Time of Imaging)

Figure 2:
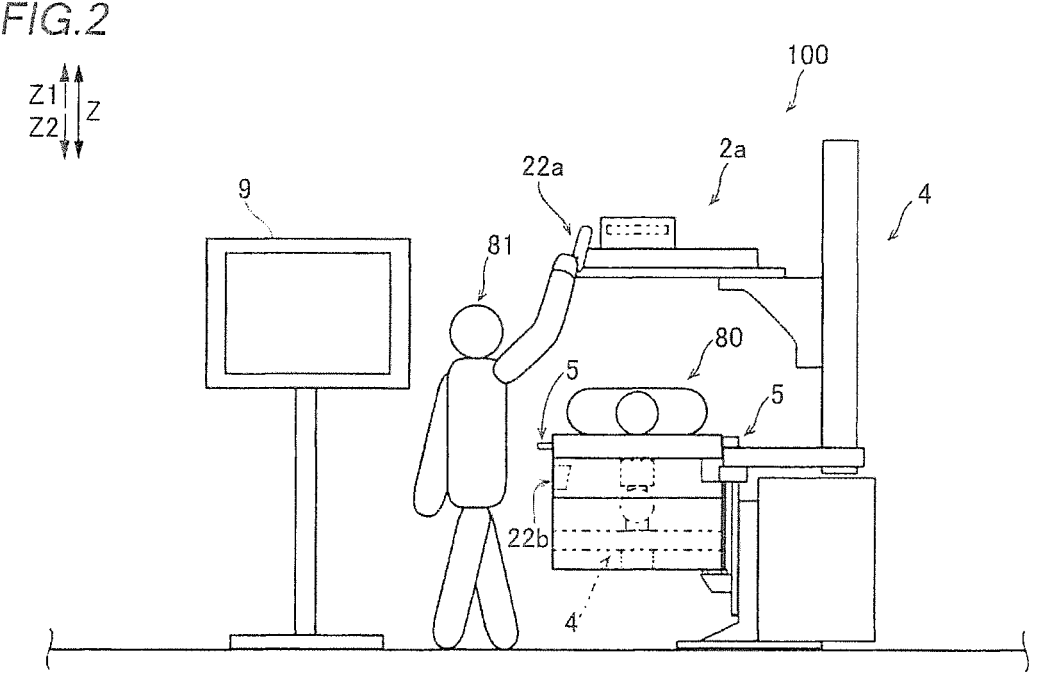
FIG. 2 is a schematic view illustrating position adjustment of an imaging system at the time of performing X-ray fluoroscopic imaging by the X-ray fluoroscopic imaging apparatus according to the embodiment.

As shown in FIG. 2, when an X-ray fluoroscopic image is captured, the operator 81 adjusts the movement of the imaging system 2 and the X-ray irradiation range in a state in which the subject 80 is placed on the table 1. Specifically, the operator 81 images the subject 80 while moving the imaging system 2 in a state in which the operator 81 grips the gripper 3. Furthermore, the operator 81 adjusts the X-ray irradiation range such that the X-ray irradiation range becomes a range suitable for a region of interest as the imaging system 2 moves. The operator 81 performs movement of the imaging system 2 and adjustment of the X-ray irradiation range while viewing the X-ray fluoroscopic image displayed on the display 9. The operator 81 repeatedly performs movement of the imaging system 2, adjustment of the irradiation range of X-rays, and imaging to image a predetermined region of interest.

(First Operation Panel)

The first operation panel 22a is now described with reference to FIG. 3. The first operation panel 22a includes an operation face plate 220 and a housing 221. The operation face plate 220 is held by the imaging system moving mechanism 4 via the housing 221. The operation face plate 220 has a rectangular shape in the plan view. In an example shown in FIG. 3, the operation face plate 220 has a rectangular shape with rounded corners.

The operation face plate 220 has an indentation 27. In the example shown in FIG. 3, the operation face plate 220 includes the indentation 27 at its substantially central position in the X direction and on the Z2 direction side. The indentation 27 has a U-shape in the plan view. The gripper 3 is connected to the housing 221 at an open end of the indentation 27.

The operation face plate 220 is provided with a plurality of operation input units 24a configured to receive operation inputs for operating the imaging system 2. The plurality of operation input units 24a are used by the operator 81 to perform input operations at the time of imaging. The plurality of operation input units 24a are used for movement of the table 1 and adjustment of the X-ray irradiation range, for example. In this embodiment, the plurality of operation input units 24a include an emergency stop unit 25a configured to receive an operation input for urgently stopping movement of the table 1 and the imaging system 2. In addition, the plurality of operation input units 24a include a stop state release unit 26a configured to receive an operation input for releasing the stop states of the table 1 and the imaging system 2. In this embodiment, each of the emergency stop unit 25a and the stop state release unit 26a is a push button configured to receive a single operation. In addition, each of operation input units 24a other than the emergency stop unit 25a and the stop state release unit 26a is also a push button configured to receive a single operation.

In this embodiment, the emergency stop unit 25a and the stop state release unit 26a are operation input units disposed on the outermost side among the plurality of operation input units 24a in the first operation panel 22a. Specifically, the emergency stop unit 25a and the stop state release unit 26a are disposed in the outermost region 11 of the first operation panel 22a. The plurality of operation input units 24a are disposed in a plurality of rows 30 in a direction (Y direction) that intersects with the longitudinal direction (X direction) of the first operation panel 22a in the plane of the first operation panel 22a. In the example shown in FIG. 3, the plurality of rows 30 include four rows of a row 30a, a row 30b, a row 30c, and a row 30d. The emergency stop unit 25a and the stop state release unit 26a are disposed in the outermost row 30a of the plurality of rows 30 in which the plurality of operation input units 24a are disposed.

Figure 3:
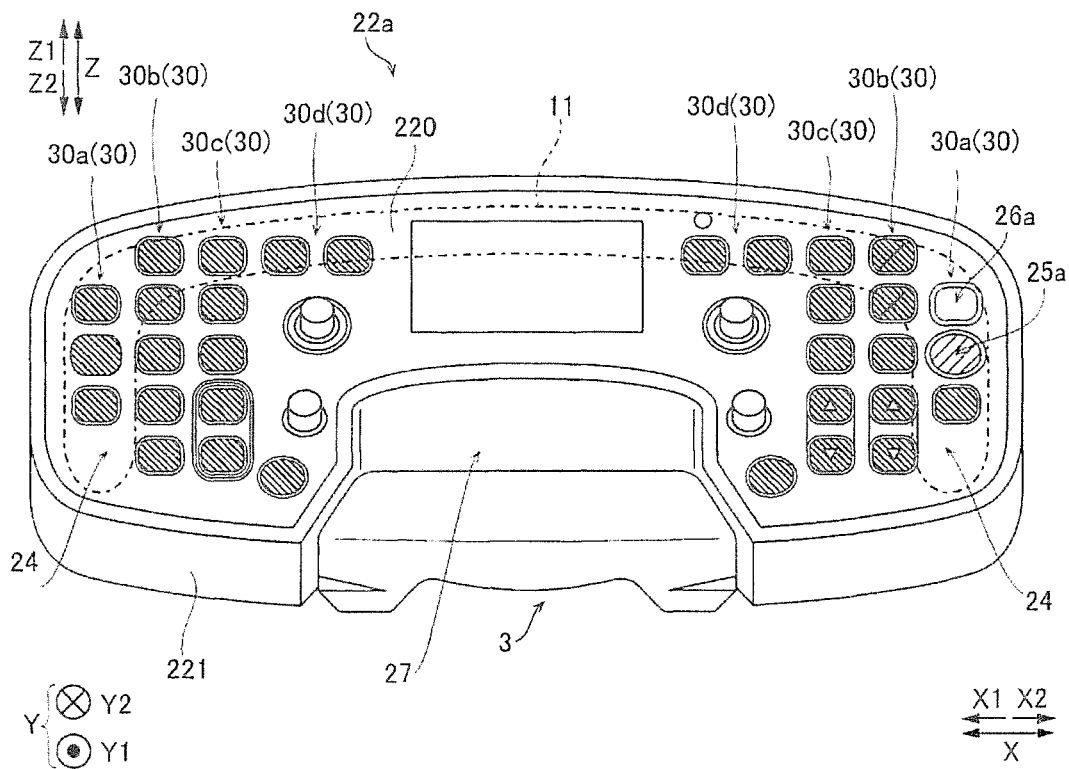
FIG. 3 is a schematic view of a first operation panel of the X-ray fluoroscopic imaging apparatus according to the embodiment.

As shown in FIG. 3, among the emergency stop unit 25a and the stop state release unit 26a, at least the emergency stop unit 25a is distinguishably different in at least one of color and shape from the remaining operation input units 24a. In the example shown in FIG. 3, the emergency stop unit 25a and the remaining operation input units 24a are distinguishably different in color and shape from each other. Furthermore, the emergency stop unit 25a and the stop state release unit 26a are distinguishably different in at least one of color and from each other. In the example shown in FIG. 3, the emergency stop unit 25a and the stop state release unit 26a are distinguishably different in color and shape from each other. Furthermore, in the example shown in FIG. 3, the stop state release unit 26a and the remaining operation input units 24a are distinguishably different in color from each other. In the example shown in FIG. 3, a difference in hatching represents a difference in color. A pressed surface 250 (see FIG. 6) of the emergency stop unit 25a is colored in red, for example. A pressed surface 260 (see FIG. 6) of the stop state release unit 26a is colored in white, for example. Furthermore, pressed surfaces of the remaining operation input units 24a are colored in black, for example. The emergency stop unit 25a has a circular shape, for example, and the area of the pressed surface 250 of the emergency stop unit 25a is larger than those of the stop state release unit 26a and the remaining operation input units 24a. The stop state release unit 26a and the remaining operation input units 24a each have a rectangular shape.

Figure 4:
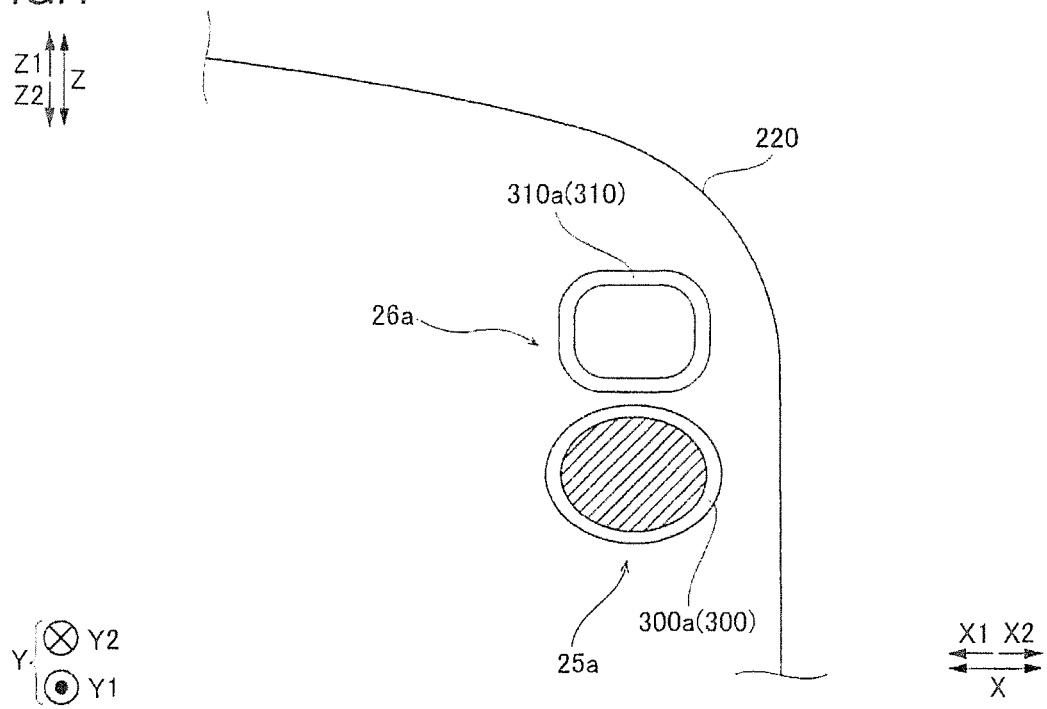
FIG. 4 is an enlarged view of a portion of the first operation panel according to the embodiment, in which an emergency stop unit and a stop state release unit are disposed.

As shown in FIG. 4, the first operation panel 22a has a surrounding region 300 around the emergency stop unit 25a and a surrounding region 310 around the stop state release unit 26a. Specifically, the first operation panel 22a has a surrounding region 300a around the emergency stop unit 25a. Furthermore, the first operation panel 22a has a surrounding region 310a around the stop state release unit 26a. The surrounding region 300 around the emergency stop unit 25a and the surrounding region 310 around the stop state release unit 26a are described below in detail.

(Second Operation Panel)

Figure 5:
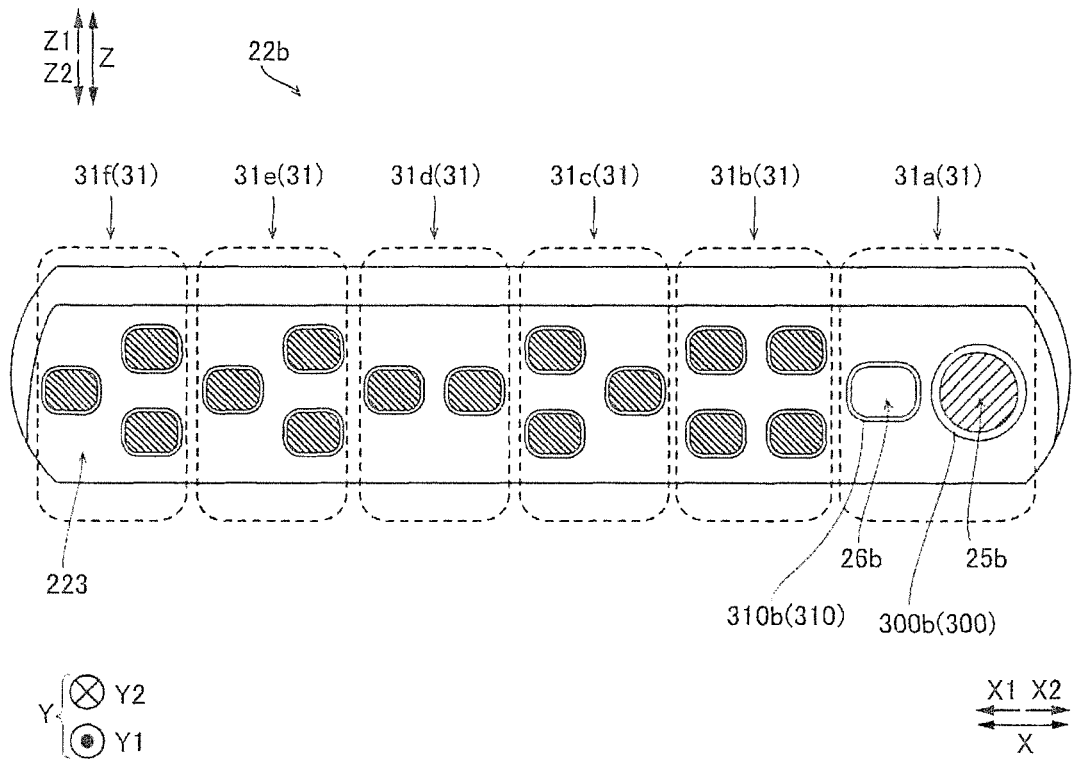
FIG. 5 is a schematic view of a second operation panel of the X-ray fluoroscopic imaging apparatus according to the embodiment.

As shown in FIG. 5, the second operation panel 22b includes a panel 223. The panel 223 is provided on the main body 10. Specifically, the panel 223 is provided in an inclined state on the main body 10. The panel 223 has a rectangular shape in the plan view. In an example shown in FIG. 5, the panel 223 has a rectangular shape with rounded corners. Similarly to the first operation panel 22a, the panel 223 is also provided with a plurality of operation input units 24b configured to receive operation inputs for operating the imaging system 2. The plurality of operation input units 24b are used for movement of the table 1 and adjustment of the X-ray irradiation range, for example. In addition, the plurality of operation input units 24b include an emergency stop unit 25b and a stop state release unit 26b. Each of the emergency stop unit 25b and the stop state release unit 26b is a push button configured to receive a single operation. In addition, each of operation input units 24b other than the emergency stop unit 25b and the stop state release unit 26b is also a push button configured to receive a single operation.

In the second operation panel 22b, the emergency stop unit 25b and the stop state release unit 26b are operation input units disposed on the outermost side among the plurality of operation input units 24. Furthermore, similarly to the plurality of operation input units 24a, the plurality of operation input units 24b are disposed in a plurality of rows 31 in a direction (Y direction) that intersects with the longitudinal direction (X direction) of the second operation panel 22b in the plane of the second operation panel 22b. In the example shown in FIG. 5, the plurality of rows 31 include six rows of a row 31a, a row 31b, a row 31c, a row 31d, a row 31e, and a row 31f. The emergency stop unit 25b and the stop state release unit 26b are disposed in the outermost row 31a among the plurality of rows 31 in which the plurality of operation input units 24b are disposed.

As shown in FIG. 5, also in the second operation panel 22b, the emergency stop unit 25b and the remaining operation input units 24b are distinguishably different in color and shape from each other. Furthermore, the emergency stop unit 25b and the stop state release unit 26b are distinguishably different in color and shape from each other. In addition, the stop state release unit 26b and the remaining operation input units 24b are distinguishably different in color from each other. Also in the example shown in FIG. 5, a difference in hatching represents a difference in color as in the example shown in FIG. 3. A pressed surface 250 (see FIG. 6) of the emergency stop unit 25b is colored in red, for example. A pressed surface 260 (see FIG. 6) of the stop state release unit 26b is colored in white, for example. Furthermore, pressed surfaces of the remaining operation input units 24b are colored in black, for example. The emergency stop unit 25b has a circular shape, for example, and the area of the pressed surface 250 of the emergency stop unit 25b is larger than those of the stop state release unit 26b and the remaining operation input units 24b. The stop state release unit 26b and the remaining operation input units 24b each have a rectangular shape.

Similarly to the first operation panel 22a, the second operation panel 22b has a surrounding region 300b around the emergency stop unit 25b and a surrounding region 310b around the stop state release unit 26b.

(Emergency Stop Unit and Stop State Release Unit)

The structure of the emergency stop unit 25 and the structure of the stop state release unit 26 are now described with reference to FIG. 6.

Figure 6:
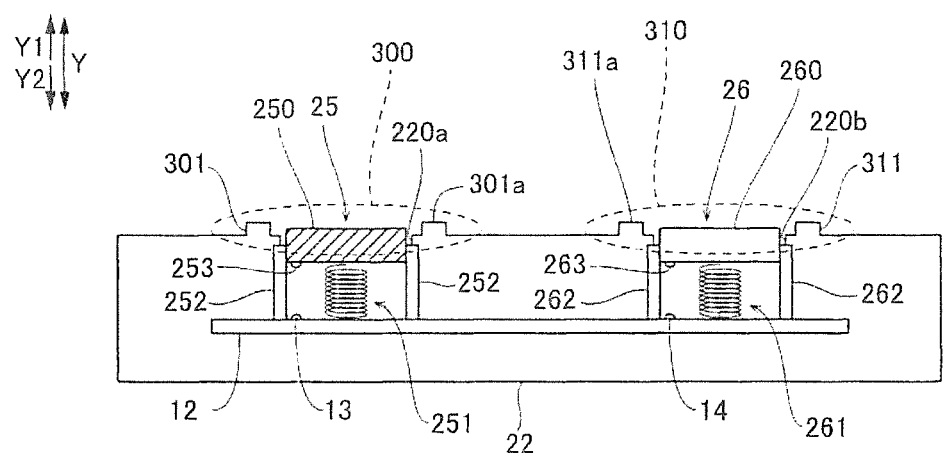
FIG. 6 is a schematic view illustrating surrounding regions according to the embodiment.

As shown in FIG. 6, the operation face plate 220 includes a base 12 to which the emergency stop unit 25 and the stop state release unit 26 are connected. The operation face plate 220 also includes an opening 220a and an opening 220b. The emergency stop unit 25 is provided in the opening 220a. The stop state release unit 26 is provided in the opening 220b. The emergency stop unit 25 and the base 12 are connected to each other by an elastic member 251. The elastic member 251 is a spring, for example. In addition, a guide member 252 is provided between the base 12 and a surface of the operation face plate 220. On a surface opposite to the pressed surface 250 of the emergency stop unit 25, a button-side contact portion 253 is provided. The base 12 is provided with a base-side contact portion 13 at a position corresponding to the button-side contact portion 253 in the X direction. When the operator 81 presses the emergency stop unit 25, the emergency stop unit 25 moves in the Y2 direction along the guide member 252. When the emergency stop unit 25 moves in the Y2 direction and the button-side contact portion 253 and the base-side contact portion 13 come into contact with each other, a signal for emergency stop is output.

The stop state release unit 26 and the base 12 are connected to each other by an elastic member 261. The elastic member 261 is a spring, for example. In addition, a guide member 262 is provided between the base 12 and the surface of the operation face plate 220. On a surface opposite to the pressed surface 260 of the stop state release unit 26, a button-side contact portion 263 is provided. The base 12 is provided with a base-side contact portion 14 at a position corresponding to the button-side contact portion 263 in the X direction. When the operator 81 presses the stop state release unit 26, the stop state release unit 26 moves in the Y2 direction along the guide member 262. When the stop state release unit 26 moves in the Y2 direction and the button-side contact portion 263 and the base-side contact portion 14 come into contact with each other, a signal for releasing the stop state is output.

(Surrounding Region Around Emergency Stop Unit and Surrounding Region Around Stop State Release Unit)

The surrounding region 300 around the emergency stop unit 25 and the surrounding region 310 around the stop state release unit 26 are now described with reference to FIG. 6. The surrounding region 300a and the surrounding region 300b have the same configuration as each other, and thus they are described as the surrounding region 300 in FIG. 6. The surrounding region 310a and the surrounding region 310b also have the same configuration as each other, and thus they are described as the surrounding region 310 in FIG. 6.

As shown in FIG. 6, the operation panel unit 22 has the surrounding region 300 around the emergency stop unit 25 and the surrounding region 310 around the stop state release unit 26. The surrounding region 300 is a region bordered with a predetermined width along the opening 220a at the peripheral edge of the opening 220a. In addition, the surrounding region 320 is a region bordered with a predetermined width along the opening 220b at the peripheral edge of the opening 220b. The pressed surface 250 of the emergency stop unit 25 and the pressed surface 260 of the stop state release unit 26 are provided at positions recessed with respect to the surrounding region 300 and the surrounding region 310 in a direction (Y direction) that intersects with a surface of the operation panel unit 22.

The surrounding region 300 and the surrounding region 310 protrude with respect to the surface of the operation panel unit 22 outside the surrounding region 300 and outside the surrounding region 310. Specifically, the surrounding region 300 includes a protrusion 301 that protrudes from the operation panel unit 22. An end 301a of the protrusion 301 protrudes in the Y1 direction with respect to the pressed surface 250 of the emergency stop unit 25. In addition, the surrounding region 310 includes a protrusion 311 that protrudes from the operation panel unit 22. An end 311a of the protrusion 311 protrudes in the Y1 direction with respect to the pressed surface 260 of the stop state release unit 26.

The surrounding region 300 and the surrounding region 310 may be integral and unitary with the operation panel unit 22, as shown in FIG. 6. In addition, the surrounding region 300 and the surrounding region 310 may be separate from the operation panel unit 22 and provided around the emergency stop unit 25 and the stop state release unit 26. The protruding height of the protrusion 301 of the surrounding region 300 in the Y direction may be any height as long as the protrusion 301 protrudes in the Y1 direction with respect to the pressed surface 250 of the emergency stop unit 25. However, when the protruding height of the protrusion 301 in the Y direction is too large, an operation on the emergency stop unit 25 becomes difficult, and it becomes difficult to thin the operation panel unit 22. Therefore, the protruding height of the protrusion 301 in the Y direction should not be too large. That is, the protruding height of the protrusion 301 in the Y direction is preferably larger than the height of the pressed surface 250 of the emergency stop unit 25, and is preferably a size that does not make it difficult to operate the emergency stop unit 25 and that allows the operation panel unit 22 to be thinned. Similarly, the protruding height of the protrusion 311 of the surrounding region 310 in the Y direction is preferably larger than the height of the pressed surface 260 of the stop state release unit 26, and is preferably a size that does not make it difficult to operate the stop state release unit 26 and that allows the operation panel unit 22 to be thinned.

Advantages of this Embodiment

According to this embodiment, the following advantages are obtained.

According to this embodiment, as described above, the X-ray fluoroscopic imaging apparatus 100 includes the table 1 on which the subject 80 is placed, the imaging system 2 including the X-ray source 20 configured to irradiate the subject 80 with X-rays and the detector 21 configured to detect the X-rays emitted from the X-ray source 20 and transmitted through the subject 80, and the operation panel unit 22 including the plurality of operation input units 24 configured to receive the operation inputs for operating the imaging system 2. Furthermore, the plurality of operation input units 24 include the emergency stop unit 25 configured to receive an operation input for urgently stopping movement of the table 1 and the imaging system 2, and the stop state release unit 26 configured to receive an operation input for releasing the stop states of the table 1 and the imaging system 2, and the emergency stop unit 25 and the stop state release unit 26 are provided separately from each other at different positions. Accordingly, the emergency stop unit 25 and the stop state release unit 26 are provided separately from each other such that each of the emergency stop unit 25 and the stop state release unit 26 can be configured as a simply structured operation input unit configured to receive an operation input only through a single operation. Consequently, it is possible to reduce the protruding height of each of the emergency stop unit 25 and the stop state release unit 26 as compared with a single operation input unit that enables two different types of operations. Therefore, the operation panel unit 22 including the emergency stop unit 25 can be thinned. Even with this structure, the emergency stop unit 25 and the stop state release unit 26 disposed at the different positions are operated separately, and thus the requirement that an emergency stop operation and an operation of releasing the stop state be taken as different intentional operations can be met.

According to this embodiment, as described above, each of the emergency stop unit 25 and the stop state release unit 26 is a push button configured to receive a single operation, the operation panel unit 22 includes the surrounding region 300 around the emergency stop unit 25 and the surrounding region 310 around the stop state release unit 26, and the pressed surface 250 of the emergency stop unit 25 and the pressed surface 260 of the stop state release unit 26 are provided at the positions recessed with respect to the surrounding region 300 and the surrounding region 310 in the direction (Y direction) that intersects with the surface of the operation panel unit 22. Accordingly, the pressed surface 250 of the emergency stop unit 25 and the pressed surface 250 of the stop state release unit 26 are disposed at the positions recessed with respect to the surrounding region 300 and the surrounding region 310 such that unintentional contact of the operator 81 with the emergency stop unit 25 and the stop state release unit 26 can be significantly reduced or prevented. Consequently, an unintentional emergency stop operation by the operator 81 can be significantly reduced or prevented, and an unintentional operation of releasing the stop state by the operator 81 can be significantly reduced or prevented. Although each of the emergency stop unit 25 and the stop state release unit 26 is configured to receive a single operation, the emergency stop unit 25 and the stop state release unit 26 are provided at the different positions such that the safety standards in which different intentional operations are required can be met.

According to this embodiment, as described above, the surrounding region 300 and the surrounding region 310 protrude with respect to the surface of the operation panel unit 22 outside the surrounding region 300 and outside the surrounding region 310. Accordingly, the surrounding region 300 and the surrounding region 310 protrude with respect to the surface of the operation panel unit 22 outside the surrounding region 300 and outside the surrounding region 310, and thus the emergency stop unit 25 and the stop state release unit 26 are disposed on the surface of the operation panel unit 22 inside the surrounding region 300 and inside the surrounding region 310 such that the pressed surface 250 of the emergency stop unit 25 and the pressed surface 260 of the stop state release unit 26 can be easily disposed at the positions recessed with respect to the surrounding region 300 and the surrounding region 310.

According to this embodiment, as described above, the operation panel unit 22 includes the first operation panel 22a integrally provided on the moving unit 2a of the imaging system 2, which is movable with respect to the table 1, and in the first operation panel 22a, the emergency stop unit 25a and the stop state release unit 26a are the operation input units disposed on the outermost side among the plurality of operation input units 24a. Accordingly, it is possible to reduce the protruding height of each of the emergency stop unit 25a and the stop state release unit 26a as compared with a single operation input unit that enables two different types of operations, and thus the emergency stop unit 25a and the stop state release unit 26a can be provided on the moving unit 2a having a limited space in which the operation input units 24a are disposed. Consequently, when the imaging system 2 moves, the emergency stop unit 25a and the stop state release unit 26a can be operated. In addition, the emergency stop unit 25a and the stop state release unit 26a are the operation input units disposed on the outermost side among the plurality of operation input units 24a such that unintentional contact of the hand (fingers) of the operator 81 who operates the operation input units 24a in order to capture an X-ray fluoroscopic image with the emergency stop unit 25a and the stop state release unit 26a can be significantly reduced or prevented when the X-ray fluoroscopic image is captured. Consequently, unintentional operations on the emergency stop unit 25a and the stop state release unit 26a by the operator 81 can be significantly reduced or prevented when the X-ray fluoroscopic image is captured.

According to this embodiment, as described above, the plurality of operation input units 24a are disposed in the plurality of rows 30 in the direction (Y direction) that intersects with the longitudinal direction of the first operation panel 22a in the plane of the first operation panel 22a, and the emergency stop unit 25a and the stop state release unit 26a are disposed in the outermost row 30a of the plurality of rows 30 in which the plurality of operation input units 24a are disposed. Accordingly, unintentional contact of the hand (fingers) of the operator 81 who operates the operation input units 24a in order to capture an X-ray fluoroscopic image with the emergency stop unit 25a and the stop state release unit 26a can be easily significantly reduced or prevented when the X-ray fluoroscopic image is captured. Consequently, unintentional operations on the emergency stop unit 25a and the stop state release unit 26a by the operator 81 can be further significantly reduced or prevented when the X-ray fluoroscopic image is captured.

According to this embodiment, as described above, the X-ray fluoroscopic imaging apparatus 100 includes the main body 10 configured to hold the table 1, the operation panel unit 22 includes the second operation panel 22b provided on the main body 10, and in the second operation panel 22b, the emergency stop unit 25b and the stop state release unit 26b are the operation input units disposed on the outermost side among the plurality of operation input units 24b. Accordingly, not only with the first operation panel 22a but also with the second operation panel 22b, an operation input for urgently stopping the X-ray fluoroscopic imaging apparatus 100 can be performed. Consequently, an operation of urgently stopping the X-ray fluoroscopic imaging apparatus 100 and an operation of releasing the stop state can be performed with the operation panel closer to the operator 81 among the first operation panel 22a and the second operation panel 22b, and thus the convenience of the operator 81 can be improved. Furthermore, in the second operation panel 22b, the emergency stop unit 25b and the stop state release unit 26b are the operation input units provided on the outermost side among the plurality of operation input units 24b such that unintentional contact of the hand (fingers) of the operator 81 who operates the operation input units 24a in order to capture an X-ray fluoroscopic image with the emergency stop unit 25b and the stop state release unit 26b can be significantly reduced or prevented when the X-ray fluoroscopic image is captured. Consequently, unintentional operations on the emergency stop unit 25b and the stop state release unit 26b by the operator 81 in the second operation panel 22b can be significantly reduced or prevented.

According to this embodiment, as described above, at least the emergency stop unit 25 of the emergency stop unit 25 and the stop state release unit 26 is distinguishably different in at least one of color and shape from the remaining operation input units 24. Accordingly, the emergency stop unit 25 can be easily distinguished from the remaining operation input units 24. Consequently, when the operator 81 performs an emergency stop operation, the emergency stop unit 25 can be distinguished from the remaining operation input units 24 at a glance, and thus the emergency stop operation can be reliably performed.

According to this embodiment, as described above, the emergency stop unit 25 and the stop state release unit 26 are distinguishably different in at least one of color and shape from each other. Accordingly, the emergency stop unit 25 and the stop state release unit 26 can be easily distinguished from each other. Consequently, when the operator 81 performs an emergency stop operation, the emergency stop unit 25 and the stop state release unit 26 can be distinguished from each other at a glance, and thus the emergency stop operation can be more reliably performed.

Modified Examples

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

Figure 7:
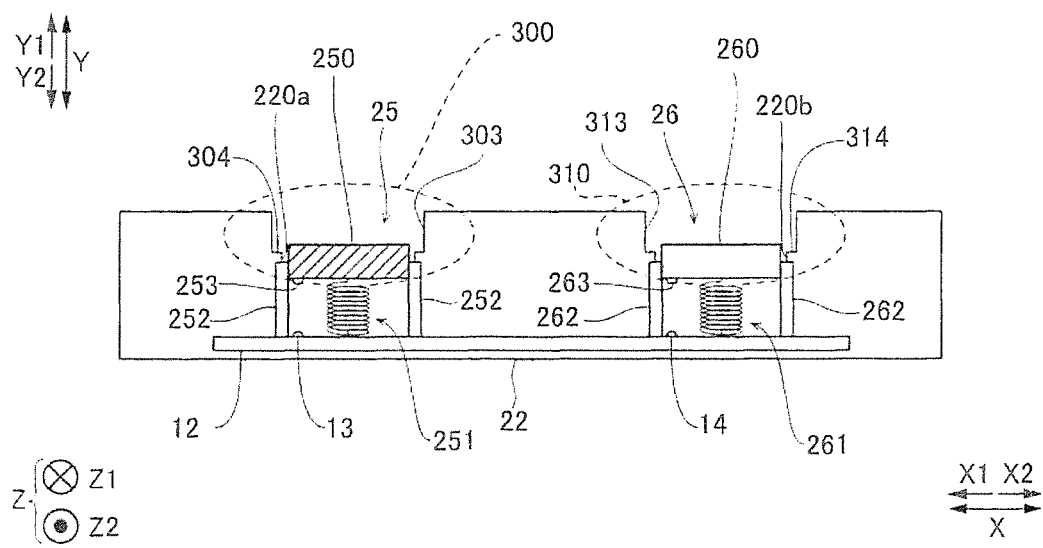
FIG. 7 is a schematic view illustrating surrounding regions according to a first modified example.

For example, while the surrounding region 300 and the surrounding region 310 protrude with respect to the surface of the operation panel unit 22 outside the surrounding region 300 and outside the surrounding region 310 in the aforementioned embodiment, the present invention is not limited to this. For example, as in a first modified example shown in FIG. 7, a surrounding region 300 and a surrounding region 310 may alternatively be recessed toward the back surface side (Y2 direction side) with respect to the surface of an operation panel unit 22 outside the surrounding region 300 and outside the surrounding region 310. Specifically, the surrounding region 300 includes a side 303 and a bottom 304. The side 303 extends in a direction (Y2 direction) in which the surrounding region 300 is recessed from the operation panel unit 22. The bottom 304 is provided on the Y2 side of the side 303, and has an opening 220*a*. An emergency stop unit 25 is provided in the opening 220*a* of the bottom 304. The length of the side 303 in a Y direction is larger than the thickness of the emergency stop unit 25. Furthermore, the surrounding region 310 includes a side 313 and a bottom 314. The side 313 extends in a direction (Y2 direction) in which the surrounding region 310 is recessed from the operation panel unit 22. The bottom 314 is provided on the Y2 side of the side 313, and has an opening 220*b*. A stop state release unit 26 is provided in the opening 220*b* of the bottom 314. The length of the side 313 in the Y direction is larger than the thickness of the stop state release unit 26. The remaining structures of the first modified example are similar to those of the aforementioned embodiment.

According to this structure, the surrounding region 300 and the surrounding region 310 are recessed toward the back surface side with respect to the surface of the operation panel unit 22 outside the surrounding region 300 and outside the surrounding region 310, and thus the emergency stop unit 25 and the stop state release unit 26 are disposed inside the surrounding region 300 and inside the surrounding region 310 such that a pressed surface 250 of the emergency stop unit 25 and a pressed surface 260 of the stop state release unit 26 can be disposed at positions recessed from the surface of the operation panel unit 22. Consequently, the pressed surface 250 of the emergency stop unit 25 and the pressed surface 260 of the stop state release unit 26 can be easily disposed at positions recessed from the surrounding region 300 and the surrounding region 310. Furthermore, the emergency stop unit 25 and the stop state release unit 26 can be disposed at the positions recessed from the surface of the operation panel unit 22, and thus as compared with the case in which the emergency stop unit 25 and the stop state release unit 26 are provided at positions that protrude from the surface of the operation panel unit 22, an erroneous operation can be further significantly reduced or prevented.

Figure 8:
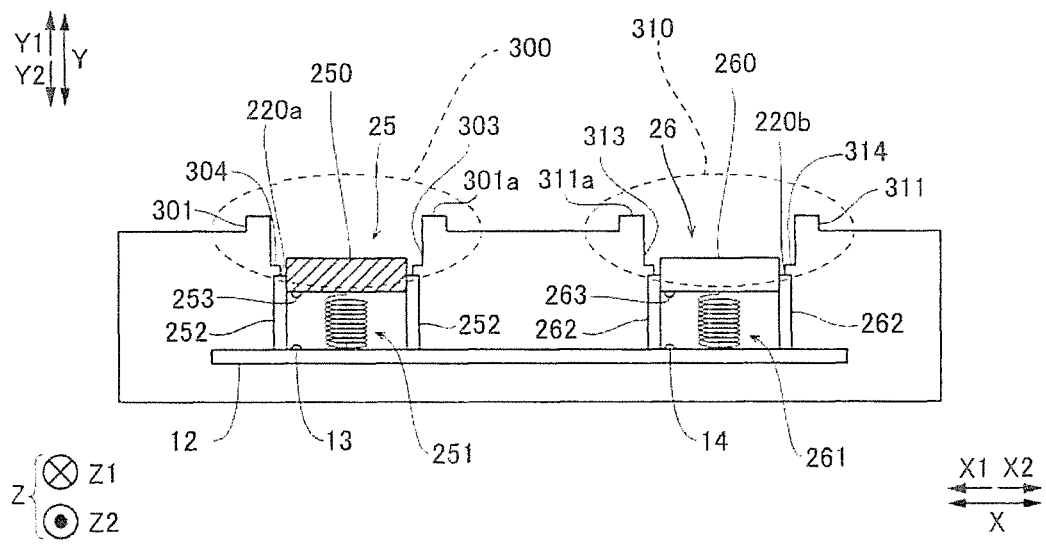
FIG. 8 is a schematic view illustrating surrounding regions according to a second modified example.

While the surrounding region 300 and the surrounding region 310 protrude from the operation panel unit 22 in the aforementioned embodiment, the present invention is not limited to this. For example, as in a second modified example shown in FIG. 8, a surrounding region 300 may alternatively include a protrusion 301, a side 303, and a bottom 304. That is, the surrounding region 300 may include a portion that protrudes from the surface of an operation panel unit 22 and a portion recessed from the surface of the operation panel unit 22 toward the back surface side. Furthermore, a surrounding region 310 may include a protrusion 311, a side 313, and a bottom 314. That is, the surrounding region 310 may include a portion that protrudes from the surface of the operation panel unit 22 and a portion recessed from the surface of the operation panel unit 22 toward the back surface side. The remaining structures of the second modified example are similar to those of the aforementioned embodiment. According to this structure, unintentional operations on the emergency stop unit 25 and the stop state release unit 26 by the operator 81 can be still further significantly reduced or prevented. Consequently, erroneous operations on the emergency stop unit 25 and the stop state release unit 26 can be still further significantly reduced or prevented.

While each of the emergency stop unit 25 and the stop state release unit 26 is a push button configured to receive a single operation in the aforementioned embodiment, the present invention is not limited to this. Each of the emergency stop unit 25 and the stop state release unit 26 may alternatively be other than a push button configured to receive a single operation. Each of the emergency stop unit 25 and the stop state release unit 26 may alternatively be a rotary operation input unit, a toggle switch operation input unit, or a rocker switch operation input unit, for example. However, when each of the emergency stop unit 25 and the stop state release unit 26 is configured as an operation input unit other than a push button configured to receive a single operation, the protruding height of each of the emergency stop unit 25 and the stop state release unit 26 is increased as compared with a push button configured to receive a single operation, and thus each of the emergency stop unit 25 and the stop state release unit 26 is preferably a push button configured to receive a single operation.

While the surrounding region 300 and the surrounding region 310 are integral and unitary with the operation face plate 220 in the aforementioned embodiment, the present invention is not limited to this. The surrounding region 300 and the surrounding region 310 may alternatively be formed by providing an end face of a so-called ring adapter configured to guide the emergency stop unit 25 and the stop state release unit 26, the end face protruding beyond the operation face plate 220.

While the operation panel unit 22 includes the first operation panel 22*a* and the second operation panel 22*b* in the aforementioned embodiment, the present invention is not limited to this. The operation panel unit 22 may alternatively include only one of the first operation panel 22*a* and the second operation panel 22*b*. In addition, the operation panel unit 22 may alternatively be provided on a console for remote control provided at a location different from that of the X-ray fluoroscopic imaging apparatus 100.

While in the first operation panel 22a, the emergency stop unit 25 and the stop state release unit 26 are operation input units disposed on the outermost side among the plurality of operation input units 24a in the aforementioned embodiment, the present invention is not limited to this. For example, the emergency stop unit 25 and the stop state release unit 26 may alternatively be operation input units disposed at positions other than the outermost side among the plurality of operation input units 24a. However, when the emergency stop unit 25 and the stop state release unit 26 are operation input units disposed at the positions other than the outermost side among the plurality of operation input units 24, the hand (finger) of the operator 81 who operates another operation input unit 24 in order to capture an X-ray fluoroscopic image may unintentionally contact the emergency stop unit 25 and the stop state release unit 26 at the time of capturing the X-ray fluoroscopic image. Therefore, the emergency stop unit 25 and the stop state release unit 26 are preferably operation input units disposed at the outermost position among the plurality of operation input units 24.

While the plurality of operation input units 24a (the plurality of operation input units 24b) are disposed in the plurality of rows 30 (the plurality of rows 31), and the emergency stop unit 25a (emergency stop unit 25b) and the stop state release unit 26a (stop state release unit 26b) are disposed in the outermost row 30a (31a) in the aforementioned embodiment, the present invention is not limited to this. For example, the emergency stop unit 25a (emergency stop unit 25b) and the stop state release unit 26a (stop state release unit 26b) may alternatively be disposed in a row other than the outermost row 30a (31a). However, when the emergency stop unit 25a (emergency stop unit 25b) and the stop state release unit 26a (stop state release unit 26b) are disposed in a row other than the outermost row 30a (31a), the hand (finger) of the operator 81 who operates another operation input unit 24a (another operation input unit 24b) in order to capture an X-ray fluoroscopic image may unintentionally contact the emergency stop unit 25a (emergency stop unit 25b) and the stop state release unit 26a (stop state release unit 26b) at the time of capturing the X-ray fluoroscopic image. Therefore, the emergency stop unit 25a (emergency stop unit 25b) and the stop state release unit 26a (stop state release unit 26b) are preferably disposed in the outermost row 30a (row 31a).

While the emergency stop unit 25 is distinguishably different in color and shape from the remaining operation input units 24 in the aforementioned embodiment, the present invention is not limited to this. The emergency stop unit 25 may alternatively be distinguishably different in one of color and shape from the remaining operation input units 24. Alternatively, the emergency stop unit 25 may not be distinguishably different from the remaining operation input units 24. However, when the emergency stop unit 25 is not distinguishably different from the remaining operation input units 24, it is difficult for the operator 81 to distinguish between the emergency stop unit 25 and the remaining operation input units 24 at a glance when the operator 81 performs an emergency stop operation, and thus the emergency stop unit 25 is preferably distinguishably different from the remaining operation input units 24.

While the emergency stop unit 25 and the stop state release unit 26 are distinguishably different in color and shape from each other in the aforementioned embodiment, the present invention is not limited to this. The emergency stop unit 25 and the stop state release unit 26 may alternatively be distinguishably different in one of color and shape from each other. Alternatively, the emergency stop unit 25 and the stop state release unit 26 may not be distinguishably different from each other. However, when the emergency stop unit 25 and the stop state release unit 26 are not distinguishably different from each other, it is difficult for the operator 81 to distinguish between the emergency stop unit 25 and the stop state release unit 26 at a glance when the operator 81 performs an emergency stop operation, and thus the emergency stop unit 25 and the stop state release unit 26 are preferably distinguishably different from each other.

While the emergency stop unit 25 is provided below the stop state release unit 26 in the plane of the first operation panel 22a in the aforementioned embodiment, the present invention is not limited to this. The emergency stop unit 25 may alternatively be provided above the stop state release unit 26. Furthermore, while the emergency stop unit 25 and the stop state release unit 26 are disposed on the right side (X2 direction side) in the plane of the first operation panel 22a in the aforementioned embodiment, the present invention is not limited to this. For example, the emergency stop unit 25 and the stop state release unit 26 may alternatively be provided on the left side (X1 direction side) in the plane of the first operation panel 22a.

While the emergency stop unit 25 is disposed on the right side (X2 direction side) of the stop state release unit 26 in the plane of the second operation panel 22b in the aforementioned embodiment, the present invention is not limited to this. For example, the stop state release unit 26 may alternatively be disposed on the right side (X2 direction side) of the emergency stop unit 25. Furthermore, while the emergency stop unit 25 and the stop state release unit 26 are disposed on the right side (X2 direction side) in the plane of the second operation panel 22b in the aforementioned embodiment, the present invention is not limited to this. For example, the emergency stop unit 25 and the stop state release unit 26 may alternatively be disposed on the left side (X1 direction side) in the plane of the second operation panel 22b.

While in the plan view, the emergency stop unit 25 has a circular shape, and the stop state release unit 26 has a rectangular shape in the aforementioned embodiment, the present invention is not limited to this. As long as the emergency stop unit 25 and the stop state release unit 26 are distinguishably different in color or the like from each other, the emergency stop unit 25 and the stop state release unit 26 may have the same shape. The emergency stop unit 25 and the stop state release unit 26 each may have any shape as long as the same are distinguishable from each other.

Figure 9:
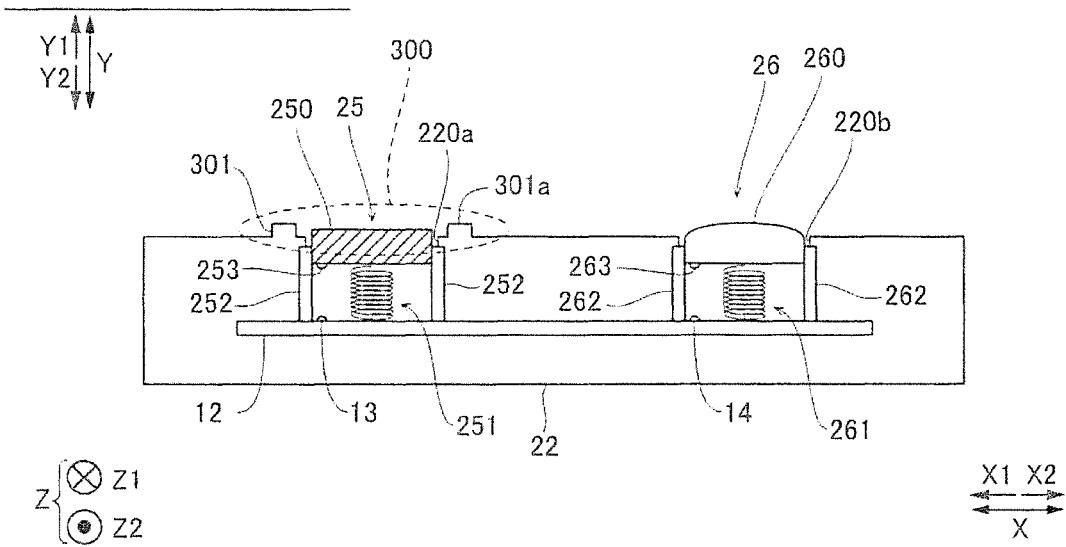
FIG. 9 is a schematic view illustrating the shape of a pressed surface of an emergency stop unit and the shape of a pressed surface of a stop state release unit according to a third modified example.

While the shape of the pressed surface 250 of the emergency stop unit 25 and the shape of the pressed surface 260 of the stop state release unit 26 are the same as each other in the aforementioned embodiment, the present invention is not limited to this. The shape of the pressed surface 250 of the emergency stop unit 25 and the shape of the pressed surface 260 of the stop state release unit 26 may alternatively be different from each other. For example, as in a third modified example shown in FIG. 9, a pressed surface 250 of an emergency stop unit 25 may have a flat plate shape, and a pressed surface 260 of a stop state release unit 26 may have a shape that protrudes in a Y1 direction. Any shape can be applied to each of the shape of the pressed surface 250 of the emergency stop unit 25 and the shape of the pressed surface 260 of the stop state release unit 26. In addition, the operation panel unit 22 may not have the surrounding region 310.

What is claimed is:

1. An X-ray fluoroscopic imaging apparatus, comprising:
a table on which a subject is placed;
an imaging system including an X-ray source configured to irradiate the subject with X-rays and a detector configured to detect the X-rays emitted from the X-ray source and transmitted through the subject; and
an operation panel unit including a plurality of operation input units configured to receive operation inputs for operating the imaging system;
wherein the plurality of operation input units include an emergency stop unit configured to receive an operation input for urgently stopping movement of the table and the imaging system, and a stop state release unit configured to receive an operation input for releasing stop states of the table and the imaging system; and
the emergency stop unit and the stop state release unit are provided separately from each other at different positions.

2. The X-ray fluoroscopic imaging apparatus, according to claim 1, wherein:
each of the emergency stop unit and the stop state release unit is a push button configured to receive a single operation;
the operation panel unit includes a surrounding region around the emergency stop unit and a surrounding region around the stop state release unit; and
a pressed surface of the emergency stop unit and a pressed surface of the stop state release unit are respectively provided at positions recessed with respect to the surrounding regions in a direction that intersects with a surface of the operation panel unit.

3. The X-ray fluoroscopic imaging apparatus, according to claim 2, wherein:
the surrounding regions protrude with respect to the surface of the operation panel unit outside the surrounding regions.

4. The X-ray fluoroscopic imaging apparatus, according to claim 2, wherein:
the surrounding regions are recessed toward a back surface side with respect to the surface of the operation panel unit outside the surrounding regions.

5. The X-ray fluoroscopic imaging apparatus, according to claim 1, wherein:
the operation panel unit includes a first operation panel integrally provided on a moving unit of the imaging system, which is movable with respect to the table; and
in the first operation panel, the emergency stop unit and the stop state release unit are operation input units disposed on an outermost side among the plurality of operation input units.

6. The X-ray fluoroscopic imaging apparatus, according to claim 5, wherein:
the plurality of operation input units are disposed in a plurality of rows in a direction that intersects with a longitudinal direction of the first operation panel in a plane of the first operation panel; and
the emergency stop unit and the stop state release unit are disposed in an outermost row of the plurality of rows in which the plurality of operation input units are disposed.

7. The X-ray fluoroscopic imaging apparatus, according to claim 5, further comprising:
a main body configured to hold the table;
wherein the operation panel unit includes a second operation panel provided on the main body; and
in the second operation panel, the emergency stop unit and the stop state release unit are the operation input units disposed on the outermost side among the plurality of operation input units.

8. The X-ray fluoroscopic imaging apparatus, according to claim 1, wherein:
at least the emergency stop unit of the emergency stop unit and the stop state release unit is distinguishably different in at least one of color and shape from remaining operation input units.

9. The X-ray fluoroscopic imaging apparatus, according to claim 8, wherein:
the emergency stop unit and the stop state release unit are distinguishably different in at least one of color and shape from each other.

* * * * *